United States Patent
Heywang et al.

(10) Patent No.: US 6,593,476 B2
(45) Date of Patent: *Jul. 15, 2003

(54) PROCESS FOR THE PREPARATION OF UV FILTER SUBSTANCES

(75) Inventors: Ulrich Heywang, Darmstadt (DE); Michael Schwarz, Weiterstadt (DE); Frank Pflücker, Darmstadt (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/887,265

(22) Filed: Jun. 25, 2001

(65) Prior Publication Data

US 2002/0013474 A1 Jan. 31, 2002

(30) Foreign Application Priority Data

Jun. 23, 2000 (DE) .......................................... 100 30 664

(51) Int. Cl.⁷ .................... C07D 235/18; C07D 235/04; C07D 403/02
(52) U.S. Cl. ................. 548/310.7; 548/304.4; 548/305.4
(58) Field of Search ................ 424/401, 60; 548/305.4, 548/304.4, 310.7

(56) References Cited

U.S. PATENT DOCUMENTS

| 5,473,079 A | 12/1995 | Heywang et al. |
| 5,585,091 A | 12/1996 | Pelzer et al. |

FOREIGN PATENT DOCUMENTS

| EP | 669323 | 2/1995 |
| WO | 93/15061 | 5/1993 |

OTHER PUBLICATIONS

Jerry March, "Advanced Organic Chemistry", 4$^{th}$ edition, 1992, John Wiley & Sons (pub.), pp. 528–529.*
International Search Report, dated Aug. 6, 2001.
Kuzuetsov, Yu V. et al., Chemical Abstracts, vol. 114, 1991 p. 732, Columbus, Ohio, US.
Houben–Weyl, Methoden der Organischen Chemie, 4. Auflage, Band 9, 1955, Thieme Verlag, Stuttgart, XP002172443, Seite 450– Seite 455.

* cited by examiner

Primary Examiner—Sreeni Padmanabhan
Assistant Examiner—Michael A. Willis
(74) Attorney, Agent, or Firm—Millen, White, Zelano & Branigan, P.C.

(57) ABSTRACT

The present invention relates to a preparation process for 2-arylbenzimidazolesulfonic acids of the formula I:

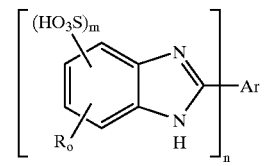

Ar is a substituted or unsubstituted phenyl or naphthyl radical and R is a $C_{1-8}$-alkyl or $C_{1-8}$-alkoxy radical. n is 1–4, m is 1–3 and o is 0–2. o-phenylenediamine is reacted in the presence of oleum with an arylcarboxylic acid or an arylcarboxylic acid derivative. Compounds prepared in this way can be used as UV filters, and as components in cosmetic compositions.

13 Claims, No Drawings

PROCESS FOR THE PREPARATION OF UV FILTER SUBSTANCES

The present invention relates to a preparation process for 2-arylbenzimidazolesulfonic acids, to the use thereof as UV filters, and to cosmetic preparations which comprise compounds prepared according to the process of the invention.

A suntan of the skin to whatever degree is regarded in today's society as attractive and as an expression of vigor and health. As well as this desired effect of the sun on the skin, however, a number of undesired secondary effects arise, such as sunburn or premature skin aging and the development of wrinkles. A number of performance UV filters have been developed which, when applied to the skin in the form of creams, lotions or gels, can effectively delay the development of sunburn even when the incidence of solar rays is relatively high.

The UV filter present in the pharmaceutical or cosmetic preparation forms a film or a layer on the surface of the skin and does not penetrate into deeper skin layers with other care substances present in the preparation. Known UV filters or sun protection agents thus act only by absorbing certain regions of sunlight, meaning that this radiation cannot penetrate into deeper layers of the skin.

As is known, the most hazardous part of solar radiation is formed by the ultraviolet (UV) rays having a wavelength of less than 400 nm. The lower limit of the ultraviolet rays which reach the surface of the earth is limited by the absorption in the ozone layer of UV rays up to about 280 nm. The sun protection filters which are currently customary in cosmetics absorb in a wavelength range from 280 to 400 nm. This range includes UV-B rays having a wavelength between 280 and 320 nm, which play a decisive role in the formation of a solar erythema. This range includes also UV-A rays having a wavelength between 320 and 400 nm, which tan the skin but also age it, favors the triggering of an erythematous reaction or can exacerbate this reaction in certain people, or can even trigger phototoxic or photoallergic and irritative reactions.

The object of skin care cosmetics is to obtain the impression of a youthful skin. In principle, there are various ways of achieving this object. For example, existing skin damage, such as irregular pigmentation or the development of wrinkles, can be smoothed out by covering powders or creams. Another approach is to protect the skin against environmental influences which lead to permanent damage and thus aging of the skin. The idea is therefore to intervene in a preventative manner and thus to delay the aging process. One example of this approach is the UV filters already mentioned which, as a result of absorption of certain wavelength regions, prevent or at least reduce skin damage. Depending on the position of their absorption maxima, UV absorbers for cosmetic and dermatological preparations are divided into UV-A and UV-B absorbers, UV-A absorbers usually also absorb in the UV-B region and are thus alternatively referred to as broad-band absorbers or broad-band filters.

Of decisive importance for the formulation is the solubility of the filter substances in both the oil and water phases since it is necessary, particularly for establishing a high protection factor, to incorporate filters into all phases of a formulation. The oil-soluble UV-B filters include isooctyl methoxycinnamate, isoamyl methoxycinnamate and methylbenzylidenecamphor. Examples of water-soluble UV filters are, in particular, the salts of 2-phenylbenzimidazole-5-sulfonic acid, the use of which as an UV ray filter has already been described in German Reichspatent No. 676 103.

Various processes are known for the preparation of arylbenzimidazolesulfonic acids. An overview of the preparation of 2-substituted benzimidazoles is given, for example, in Chemical Reviews Vol. 74, No. 3, 1974 p. 279 et seq., e.g., the preparation according to V. G. Sayapin et al., KhGC [Chemistry of Heterocyclic Compounds] 6, 1970 630–632. The method therein takes place in a two-stage reaction in which 2-phenylbenzimidazole is prepared by either reaction 1,2-phenylenediamine and the bisulfite adduct of benzaldehyde, or by reacting phenylenediamine and benzoic acid in the presence of polyphosphoric acid. The 2-phenylbenzimidazole is then reacted with chlorosulfonic acid.

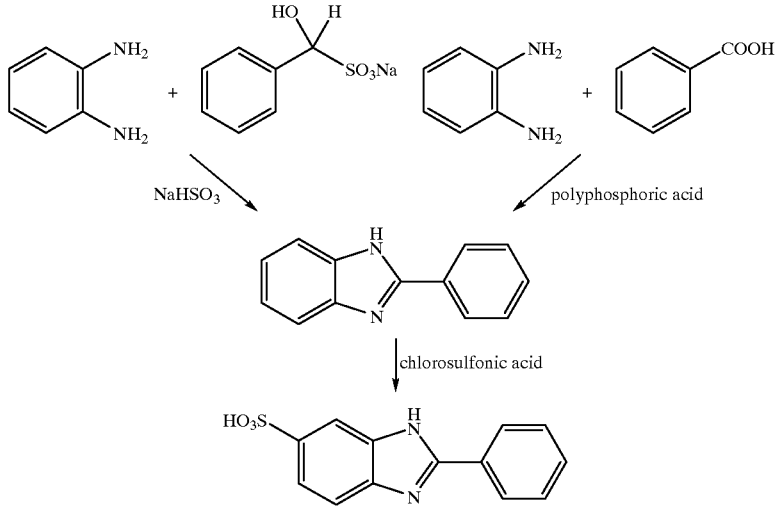

However, this process has big disadvantages:
It is a two-stage process and is thus complex and expensive.
In the first preparation process of phenylbenzimidazole sodium hydrogensulfite must be used in large excess so that large amounts of sulfur dioxide are freed in the course of the work-up,
1-benzyl-2-phenylbenzimidazole may form as by-product, which can only be separated off with difficulty,
elemental sulfur is produced as by-product in colloidal, finely divided form which may pass into the end product.

In the second process of the preparation of phenylbenzimidazole from benzoic acid, phosphoric acid passes into the waste water, which is undesired because of eutrophication in lakes and rivers.

International application WO 93/15061 describes a process in which monosulfonated products are obtained directly in a single-stage process by the reaction of o-phenylenediamine with arylcarboxylic acids in 96% sulfuric acid as solvent.

The use of chlorosulfonic acid for the preparation of bisbenzimidazoloylsulfonic acids in a single-stage process is described in European patent application EP-A-669 323. Here, double sulfonation of the benzimidazole units is achieved by the chlorosulfonic acid. However, various problems are associated with the use of chlorosulfonic acid:

gas (HCl) is evolved during the reaction, making pressure regulation necessary, collection and disposal of the aggressive and toxic gas (HCl) is required, extremely corrosion-resistant apparatuses are required for the chloride-containing sulfuric acid which is formed, recycling of the chloride-containing sulfuric acid resulting from the use of chlorosulfonic acid is only possible with difficulty.

There is therefore a need for an alternative process for the preparation of arylbenzimidazolesulfonic acids, in particular of at least disulfonated arylbenzimidazolesulfonic acids in which the problems discussed above do not arise.

It has now surprisingly been found that the preparation of said arylbenzimidazolesulfonic acid is possible using oleum instead of chlorosulfonic acid, avoiding the abovementioned problems.

The present invention provides a process for the preparation of 2-arylbenzimidazolesulfonic acids of the formula I

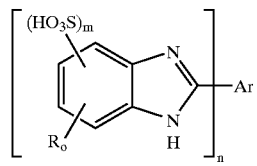

I in which Ar is a substituted or unsubstituted phenyl or naphthyl radical and R is a $C_{1-8}$-alkyl or $C_{1-8}$-alkoxy radical, n is 1, 2, 3 or 4, m is 1, 2 or 3 and o is 0, 1 or 2. In this process, a o-phenylenediamine according to formula II

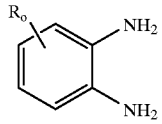

II is reacted in the presence of sulphuric acid activated by oleum (activated sulfuric acid) with a compound according to formula III

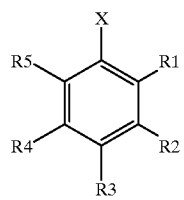

III where R1, R2, R3, R4 and R5, in each case independently of one another, are a radical such as an H, $C_{1-8}$-alkyl, $C_{1-8}$-alkoxy, hydroxyl, nitro, F, Cl, Br, I, COOH, COOR', COCl, COBr or CN radical, X is a radical such as a —COOH, —COOR', —COCl, —COBr, or —CN radical. R1 and R2 together, or R2 and R3 together, may also be a fused-on, optionally substituted phenylene unit, and R' is a $C_{1-20}$-alkyl radical. Examples of substituents of the phenylene unit are the same which define the radicals for R1, R2, R3, R4 and R5.

The use of oleum (sulfur trioxide) for the activation of the sulfuric acid has various advantages compared with the use of chlorosulfonic acid:

gas (HCl) is not evolved during the reaction, meaning that pressure regulation is not necessary, accordingly, the collection and disposal of the aggressive gas (HCl) is not required, while extremely corrosion-resistant apparatuses is required to handle the chloride-containing sulfuric acid which is formed when chlorosulfonic acid is used, the process with oleum can be carried out with less complex equipment, after hydrolysis of the oleum, sulfuric acid is present which can be recycled with relative ease, while the recycling of the chloride-containing sulfuric acid resulting from the use of chlorosulfonic acid is only possible with difficulty.

For purposes of the present invention, 2-arylbenzimidazolesulfonic acids should also be understood as meaning the salts of these acids. The salts are preferably being the alkali metal salts, in particular the sodium or potassium salts, or the ammonium salts, in particular the triethanolammonium salts of the corresponding sulfonic acids. The preparation of these salts from the acids is usually carried out by reacting the sulfonic acid with a base, such as sodium hydroxide solution, potassium hydroxide solution, or an amine. This process does not present any difficulties at all to the person skilled in the art and may expressly be a constituent of the process according to the invention.

Here, it is preferred according to the invention if arylbenzimidazolesulfonic acids are prepared which have been sulfonated twice or three times, preferably twice on each benzimidazole ring; i.e., compounds of the formula I where m is 2 are prepared. According to the invention, particular preference is given, for example, to a process for the preparation of 2-phenylbenzimidazole-4,6-disulfonic acid (formula Ia; where, the betaine form usually present in the case of benzimidazolesulfonic acids is indicated); 1,4-bis(2-benzimidazoloyl)benzene-4,4',6,6'-tetrasulfonic acid (formula Ib; corresponds to 2,2'-(1,4-phenylene)bis-1H-benzimidazole-4,6-disulfonic acid); or 1,3,5-tris(2-benzimidazoloyl)benzene-4,4',4'',6,6',6''-tetrasulfonic acid (formula Ic; corresponds to 2,2',2''-(1,3,5-phenylene)bis-1H-benzimidazole-4,6-disulfonic acid). Using the process according to the invention it is, however, also possible, with appropriate choice of the reaction conditions, to prepare 2,2'-(1,4-phenylene)bis-1H-benzimidazole-5-sulfonic acid (formula Id; corresponds to 1,4-bis(2-benzimidazoloyl)benzene-5,5-disulfonic acid).

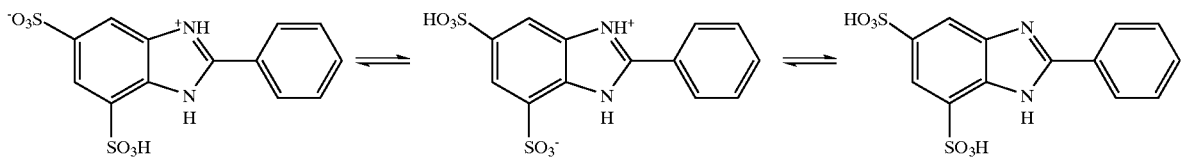

Ia

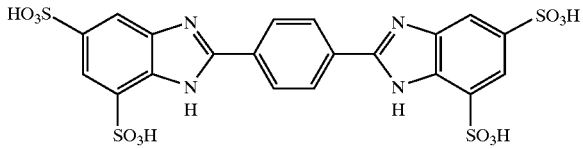

Ib

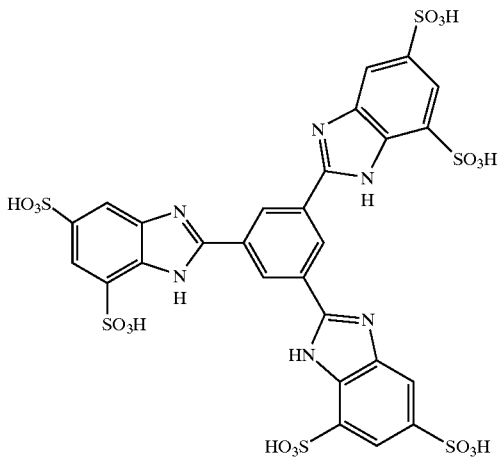

Ic

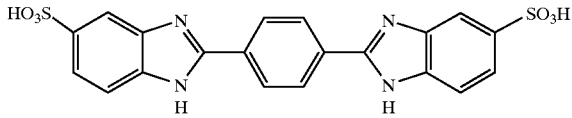

Id

Here, the sulfonation can be controlled via the reaction conditions. In particular, to achieve double sulfonation on each benzimidazole ring, it is preferred that oleum is used in an amount and concentration which permits double sulfonation. Just for the ring closure to benzimidazole from the o-phenylenediamine using a carboxylic acid, two moles of sulfur trioxide are consumed per mole of o-phenylenediamine. For each sulfonation, 1 sulfur trioxide is in turn consumed, meaning that for a disulfonation at least 4 mol of sulfur trioxide must be present per mole of o-phenylenediamine. Accordingly, a large amount of oleum must therefore be used.

The reaction is usually carried out at temperatures from 20° C. to 200° C., preferably from 160° C. to 190° C. The reaction temperature is usually maintained for 2 to 8 hours; at reaction times of less than 2 hours, monosulfonation products are still observed, which can only be separated off from the preferred, disulfonated product with difficulty.

In regard to the compound of formula III, it is preferable according to the invention if the group X in compound III is a —COOH group or a —COOR' group, where R' is a $C_{1-20}$-alkyl radical. R' is preferably a $C_{1-8}$-alkyl radical and particularly preferably a methyl or ethyl radical, and the compound is preferably chosen from the group consisting of benzoic acid, salicylic acid, phthalic acid, terephthalic acid, isophthalic acid, 1,2,3-benzenetricarboxylic acid, 1,2,4-benzenetricarboxylic acid, 1,3,5-benzenetricarboxylic acid, 1,2,4,5-benzenetetracarboxylic acid, 1-naphthalenecarboxylic acid, 2-naphthalenecarboxylic acid, or 3-naphthalenecarboxylic acid. Preferably, benzoic acid, terephthalic acid, phthalic acid or 1,3,5-benzenetricarboxylic acid is used as compound III in the process according to the invention.

Implementation of the process according to the invention is straightforward and does not present difficulties to the person skilled in the art. A preferred variant for carrying out the reaction is given below. This may serve as an example, but does not limit the possible variants for carrying out the reaction:

The sulfuric acid, preferably in the form of a 50–100% solution, and in particular as a concentrated approximately 96% solution, is introduced and the ortho-phenylenediamine or derivative thereof is introduced. Activation with oleum (e.g., a 65% solution of sulfur trioxide in sulfuric acid) is then carried out, the temperature preferably being maintained below 150° C. Here, the amount of sulfur trioxide is chosen such that all of the water liberated during the reaction can be collected, i.e., for the preparation of a benzimidazoledisulfonic acid, at least 4 mol of sulfur trioxide are used per mole of o-phenylenediamine.

The addition of the second reactant (such as an arylcarboxylic acid or arylcarboxylic acid derivative) is preferably only carried out for safety reasons after cooling to a temperature below 100° C. since the temperature of the reaction mixture may increase further as the result of the addition. The arylcarboxylic acid is preferably used in a molar ratio to the phenylenediamine in which the aryl unit is relative to the benzimidazole units in the target molecule; i.e., for the preparation of monobenzimidazolebenzene derivatives, an arylmonocarboxylic acid or an arylmonocarboxylic acid derivative is used in the ratio of about 1:1 with o-phenylenediamine. For the preparation of bisbenzimidazolebenzene derivatives, an aryldicarboxylic acid or an aryldicarboxylic acid derivative is used in the ratio of about 1:2 with o-phenylenediamine. For the preparation of trisbenzimidazolebenzene derivative, an aryltricarboxylic acid or an aryltricarboxylic acid derivative is used in the ratio of about 1:3 with o-phenylenediamine.

The reaction mixture is then slowly heated, preferably to a temperature from 150 to 250° C., were preferably from 160 to 200° C., and maintained at this temperature for, preferably 2 to 8 hours; optionally with stirring. The reaction mixture is then cooled, preferably to temperatures below 10° C., and water is added for the hydrolysis.

The mixture is stirred briefly, preferably from 20 minutes to 2 hours. Then the solid constituents are separated off, preferably washed with warm water, and dried.

To purify the dried crude product, it is preferably dissolved in sodium hydroxide solution, and the resulting solution is purified, preferably with activated carbon. The end-product is precipitated out of the colorless solution using an acid, preferably a mineral acid such as sulphuric acid.

Because of their absorption maxima in the UV region, the 2-arylbenzimidazolesulfonic acids according to the invention are suitable as UV filter substances. Here, it is found that the 2-phenylbenzimidazolesulfonic acids prepared according to the invention absorb in the UV-B region, while the bis- and trisbenzimidazoyl compounds prepared according to the invention are broad-band filters which absorb both in the UV-A region and in the UV-B region.

Accordingly, the present invention further provides for the use of a 2-arylbenzimidazolesulfonic acid according to the invention as UV filter. Because of this use option, the substances prepared according to the process of the invention are highly suitable for use in cosmetic formulations. The invention thus further relates to cosmetic formulations having UV protection properties which comprise at least one compound prepared according to the invention.

The protective action of these formulations against UV radiation can be improved if the formulation comprises one or more further UV filters in addition to the UV filter according to the invention.

In principle, all UV filters are suitable for a combination with the compound of the invention. Particular preference is given to those UV filters whose physiological safety has already been demonstrated. There are many tried and tested substances known from the specialist literature both for UVA and also UVB filters such as:

benzylidenecamphor derivatives, such as 3-(4'-methylbenzylidene)-dl-camphor (e.g., Eusolex® 6300), 3-benzylidenecamphor (e.g., Mexoryl® SD), polymers of N-{(2 and 4)-[(2-oxoborn-3-ylidene) methyl]benzyl}acrylamide (e.g., Mexoryl® SW), N,N, N,-trimethyl-4-(2-oxoborn-3-ylidenemethyl)anilinium methylsulfate (e.g., Mexoryl® SK) or α-(2-oxoborn-3-ylidene)toluene-4-sulfonic acid (e.g., Mexoryl® SL), benzoylmethanes or dibenzoylmethanes, such as 1-(4-tert-butylphenyl)-3-(4-methoxyphenyl)propane-1,3-dione (e.g., Eusolex® 9020) or 4-isopropyldibenzoylmethane, benzophenones, such as 2-hydroxy-4-methoxy-benzophenone (e.g., Eusolex® 4360) or 2-hydroxy-4-methoxybenzophenone-5-sulfonic acid and its sodium salt (e.g., Uvinul® MS-40), methoxycinnamic esters, such as octyl methoxycinnamate (e.g., Eusolex® 2292), isopentyl 4-methoxycinnamate, e.g., as a mixture of the isomers (e.g., Neo Heliopan® E 1000), salicylate derivatives, such as 2-ethylhexyl salicylate (e.g., Eusolex® OS), 4-isopropylbenzyl salicylate (e.g., Megasol®) or 3,3,5-trimethylcyclohexyl salicylate (e.g., Eusolex® HMS), 4-aminobenzoic acid and derivatives, such as 4-aminobenzoic acid, 2-ethylhexyl 4-(dimethylamino) benzoate (e.g., Eusolex® 6007), ethoxylated ethyl 4-aminobenzoate (e.g., Uvinul® P25), further benzimidazole derivatives, such as 2-phenylbenzimidazole-5-sulfonic acid, and its potassium, sodium, lithium, ammonium and triethanolamine salts (e.g., Eusolex® 232), 2,2'-(1,4-phenylene) bis(1H-benzimidazole-4,6-disulfonic acid, monosodium salt) (CAS No. 180 898-37-7) and 2,2'-(1,4-phenylene)bis(1H-benzimidazole-5-sulfonic acid) and its potassium, sodium and triethanolamine salts and further substances, such as 2-ethylhexyl 2-cyano-3,3-diphenylacrylate (e.g., Eusolex® OCR), 3,3-(1,4-phenylenedimethylene)bis(7,7-dimethyl-2-oxobicyclo-[2.2.]hept-1-ylmethanesulfonic acid, and its salts (e.g., Mexoryl® SX), 2,4,6-trianilino-(p-carbo-2'-ethylhexyl-1'-oxy)-1,3,5-triazine (e.g., Uvinul® T 150), 2-(2H-benzotriazole-2-yl)-4-methyl-6-(2-methyl-3-(1,3,3,3-tetramethyl-1-(trimethylsilyloxy) disiloxanyl)-propyl)phenol (e.g., Silatriazole®), 4,4'-[(6-[4-((1,1,-dimethylethyl)aminocarbonyl) phenylamino]-1,3,5-triazine-2,4-diyl)diimino]bis (benzoic acid 2-ethylhexyl ester) (e.g., Uvasorb® HEB), α-trimethylsilyl)-ω-[trimethylsilyl)oxy]poly [oxy-(dimethyl [and approximately 6% methyl[2-[p-[2, 2-bis(ethoxycarbonyl]vinyl]phenoxy]-1-methyleneethyl] and about 1.5% methyl[3-[p-2,2-bis (ethoxycarbonyl)vinyl)phenoxy)propenyl) and 0.1 to 0.4% (methylhydrogen)silylene]] (n≈60) (CAS No. 207 574-74-1), 2,2'-methylenebis(6-(2H-benzotriazole-2-yl)-4-(1,1,3,3-tetramethylbutyl) phenol) (CAS No. 103 597-45-1) and 2,4-bis{[4-(2-ethylhexyloxy)-2-hydroxy]phenyl}-6-(4-methoxyphenyl)-1,3,5-triazine (CAS No 103 597-45-[lacuna], 187 393-00-6).

The compounds given in the list are only to be regarded as examples, as it is of course possible to use other UV filters. The organic UV filters above are, like the 2-arylbenzimidazolesulfonic acids prepared according to the invention, usually incorporated into cosmetic formulations in an amount of from 0.5 to 20% by weight, based on the weight of the formulation, preferably in an amount of 1–15% by weight and particularly preferably in an amount of from 2 to 8% by weight per individual substance. Overall, the cosmetic preparations usually comprise up to 40% by weight, preferably 5 to 25% by weight, of such organic UV filters, which include the total of the filter substance of the invention and any additional organic filter substances.

Conceivable inorganic UV filters are those from the group of titanium dioxides, such as, for example, coated titanium dioxide (e.g., Eusolex® T-2000, Eusolex® T-AQUA), zinc oxides (e.g., Sachtotec®), iron oxides and cerium oxides. These inorganic UV filters are usually incorporated into cosmetic formulations in an amount of from 0.5 to 20 percent by weight based on the weight of the total formulation, preferably 2–10%.

If various inorganic or organic UV filters are used, then these can be used in virtually any ratios relative to one another. The ratios of the individual substances to one another are usually in the range 1:10–10:1, preferably in the range 1:5–5:1 and particularly preferably in the range 1:2–2:1. If UV-A filters are used in addition to UV-B filters, then it is advantageous for most applications and therefore preferred according to the invention if the proportion of UV-B filters predominates and the ratio of UV-A filters: UV-B filters is in the range 1:1 to 1:3.

In addition to the 2-arylbenzimidazolesulfonic acids according to the invention, preferred compounds having UV-filtering properties for the cosmetic preparations are 3-(4'-methylbenzylidine)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate and coated titanium dioxide.

The protecting action against oxidative stress or against the effect of free radicals can be further improved if the formulation comprises one or more antioxidants.

There are many tried and tested substances known from the specialist literature which can be used for the antioxidant, e.g., amino acids (e.g., glycine, histidine, tyrosine, tryptophan) and derivatives thereof, imidazoles (e.g., urocanic acid) and derivatives thereof, peptides, such as D,L-carnosine, D-carnosine, L-carnosine and derivatives thereof (e.g., anserine), carotinoids, carotenes (e.g., α-carotene, β-carotene, lycopene) and derivatives thereof, chlorogenic acid and derivatives thereof, lipoic acid and derivatives thereof (e.g., dihydrolipoic acid), aurothioglucose, propylthiouracil and other thiols (e.g., thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glycerylesters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g., buthionine-sulfoximine, homocysteine-sulfoximine, buthionine-sulfone, penta-, hexa- and heptathionine-sulfoximine) in very low tolerated doses (e.g., pmol to µmol/kg), and also (metal) chelating agents, (e.g., α-hydroxy fatty acids, palmitic acid, phytic acid, lactoferrin), α-hydroxy acids (e.g., citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (e.g., ascorbyl palmitate, magnesium ascorbyl phosphate, ascorbyl acetate), tocopherols and derivatives (e.g., vitamin E acetate), vitamin A and derivatives (e.g., vitamin A palmitate), and coniferyl benzoate of benzoin resin, rutin and salts of the sulfuric ester of rutin and derivatives thereof, α-glycosyl rutin, ferulic acid, furfurylidineglucitol, carosine, butylhydroxy-toluene, butylhydroxyanisol, nordihydroguaretic acid, trihydroxybutyrophenone, quercetin, uric acid and derivatives thereof, mannose and derivatives thereof, zinc and derivatives thereof (e.g., ZnO, $ZnSO_4$), selenium and derivatives thereof (e.g., selenomethionine), and stilbenes and derivatives thereof (e.g., stilbene oxide, trans-stilbene oxide).

Mixtures of antioxidants are likewise suitable for use in the cosmetic formulations according to the invention. Known and commercial mixtures are, for example, mixtures comprising, as active ingredients, lecithin, L-(+)-ascorbyl palmitate and citric acid (e.g., Oxynex® AP), natural tocopherols, L-(+)-ascorbyl palmitate, L-(+)-ascorbic acid and citric acid (e.g., Oxynex® K LIQUID), tocopherol extracts from natural sources, L-(+)-ascorbyl palmitate, L-(+)-ascorbic acid and citric acid (e.g., Oxynex® L LIQUID), DL-α-tocopherol, L-(+)-ascorbyl palmitate, citric acid and lecithin (e.g., Oxynex® LM) or butylhydroxytoluene (BHT), L-(+)-ascorbyl palmitate and citric acid (e.g., Oxynex® 2004).

The formulations according to the invention can comprise vitamins as further ingredients. Preferably, vitamins and vitamin derivatives chosen from vitamin A, vitamin A propionate, vitamin A palmitate, vitamin A acetate, retinol, vitamin B, thiamine chloride hydrochloride (vitamin $B_1$), riboflavin (vitamin $B_2$) nicotinamide, vitamin C (ascorbic acid), vitamin D, ergocalciferol (vitamin $D_2$), vitamin E, DL-α-tocopherol, tocopherol E acetate, tocopherol hydrogen-succinate, vitamin $K_1$, esculin (vitamin P active ingredient), thiamine (vitamin $B_1$) nicotinic acid (niacin), pyridoxine, pyridoxal, pyridoaxmine, (vitamin $B_6$), panthothenic acid, biotin, folic acid and cobalamine (vitamin $B_{12}$) are present in the cosmetic formulations according to the invention. Vitamin A palmitate, vitamin C, DL-α-tocopherol, tocopherol E acetate, nicotinic acid, panthothenic acid and biotin are particularly preferred.

The compounds prepared according to the invention can be incorporated into cosmetic formulations in the customary manner. Suitable formulations are those for external use, such as cream, lotion, gel or as a solution which can be sprayed onto the skin. In this respect, it is preferred if the preparation comprises at least one oil phase and at least one water phase, the 2-arylbenzimidazolesulfonic acid prepared according to the invention being present in at least one aqueous phase.

Examples of application forms of the cosmetic or pharmaceutical formulations according to the invention which may be mentioned are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any customary carriers, auxiliaries and optionally further active ingredients may be added to the formulation.

Preferred auxiliaries originate from the group of preservatives, antioxidants, stabilizers, solubility promoters, vitamins, colorants, odour improvers.

Ointments, pastes, creams and gels may comprise the customary carriers, e.g., animal and vegetable fats, waxes, paraffins, starch, tragacanth, cellulose derivatives, polyethylene glycols, silicones, bentonites, silica, talc and zinc oxide or mixtures of these substances.

Powders and sprays may comprise the customary carriers, e.g., lactose, talc, silica, aluminium hydroxide, calcium silicate and polyamide powder or mixtures of these substances. Sprays can additionally comprise customary propellants, e.g., chlorofluorocarbons, propane/butane or dimethyl ether.

Solutions and emulsions can comprise the customary carriers, such as solvents, solubility promoters and emulsifiers, e.g., water, ethanol, isopropanol, ethyl carbonate, ethyl acetate, benzyl alcohol, benzyl benzoate, propylene glycol, 1,3-butylglycol, oils, in particular cotton seed oil, peanut oil, wheatgerm oil, olive oil, castor oil and sesame oil, glycerol fatty acid ester, polyethylene glycols and fatty acid esters of sorbitan or mixtures of these substances.

Suspensions can comprise the customary carriers such as liquid diluents, e.g., water, ethanol or propylene glycol, suspending agents, e.g., ethoxylated isostearyl alcohols, polyoxyethylene sorbitol esters and polyoxyethylene sorbitan esters, microcrystalline cellulose, aluminium metahydroxide, bentonite, agar agar and tragacanth or mixtures of these substances.

Soaps can comprise the customary carriers, such as alkali metal salts of fatty acids, salts of fatty acid mono esters, fatty acid protein hydrolysates, isethionates, lanolin, fatty alcohol, vegetable oils, plant extracts, glycerol, sugars or mixtures of these substances.

Surfactant-containing cleansing products can comprise the customary carrier substances, such as salts of fatty alcohol sulfates, fatty alcohol ether sulfates, sulfosuccinic monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

Face and body oils can comprise the customary carrier substances such as synthetic oils, such as fatty acid esters, fatty alcohols, silicone oils, natural oils, such as vegetable oils and oily plant extracts, paraffin oils, lanolin oils or mixtures of these substances.

Further typically cosmetic application forms are also lipsticks, lipcare sticks, mascara, eyeliner, eyeshadow, blusher, powder make-up, emulsion make-up and wax make-up, and sunscreen, presun and aftersun preparations.

All compounds or components which can be used in the cosmetic formulations are either known and available commercially or can be synthesized by known processes.

The cosmetic preparation according to the invention is particularly suitable for protecting human skin against the harmful influences of the UV constituents in sunlight, in addition they also offer protection against aging processes of the skin and against oxidative stress, i.e. against damage caused by free radicals, as are produced, for example, by solar irradiation, heat or other influences. In this connection, they are in various use forms customarily used for this application. For example, it may in particular be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The formulation may comprise cosmetic adjuvants which are customarily used in this type of preparation, such as, for example, thickeners, softeners, moisturizers, surface-active agents, emulsifiers, preservatives, antifoams, perfumes, waxes, lanolin, propellants, dyes and/or pigments which color the composition itself or the skin, and other ingredients customarily used in cosmetics.

As dispersant or solubilizer it is possible to use an oil, wax or other fatty substance, a lower monoalcohol or a lower polyol or mixtures thereof. Preferred monoalcohols or polyols include ethanol, isopropanol, propylene glycol, glycerol and sorbitol.

A preferred embodiment of the invention is an emulsion in the form of a protective cream or milk and which, apart from the 2-arylbenzimidazolesulfonic acids prepared according to the invention and preferably further UV filters, comprise, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The cosmetic preparation according to the invention can also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes are usually used.

The cosmetic formulation can also be used to protect the hair against photochemical damage in order to prevent changes of color shades, decoloration or damage of a mechanical nature. In this case, a suitable formulation is in the form of a shampoo, lotion, gel or emulsion for rinsing out, the formulation in question being applied before or after shampooing, before or after coloring or bleaching or before or after permanent waving. It is also possible to choose a formulation in the form of a lotion or gel for styling or treating the hair, in the form of a lotion or gel for brushing or blow-waving, in the form of a hair lacquer, permanent waving composition, colorant or bleach for the hair. Apart from the 2-aryl-benzimidazolesulfonic acid(s) according to the invention and further UV filters, the cosmetic formulation may comprise various adjuvants used in this type of composition, such as surface-active agents, thickeners, polymers, softeners, preservatives, foam stabilizers, electrolytes, organic solvents, silicone derivatives, oils, waxes, antigrease agents, dyes and/or pigments which color the composition itself or the hair, or other ingredients customarily used for hair care.

The cosmetic preparations according to the invention can be prepared using techniques which are well known to the person skilled in the art.

To protect the skin and/or natural or sensitized hair against solar rays, a cosmetic preparation comprising one or more compounds prepared according to the invention is applied to the skin or the hair. Sensitized hair is understood here as meaning hair which has been subjected to a chemical treatment, such as a permanent waving treatment, a coloring process or bleaching process.

In addition, the 2-arylbenzimidazolesulfonic acids prepared according to the invention also have a stabilizing effect on the formulation. When used in corresponding products, the latter are thus also stable for longer and do not change their appearance. In particular, even in the case of longer-lasting application or relatively long storage, the effectiveness of the ingredients, e.g., vitamins, is retained. This is particularly advantageous in the case of compositions for protecting the skin against the effect of UV rays since these cosmetics are exposed to particularly high stresses by UV radiation.

The invention further provides for the stabilization of particular UV filters. A known and high-performance class of light protection filter substances is formed by the dibenzoylmethane derivatives. However, a disadvantage is that these substances are very readily decomposed by UV light and thus their protecting properties are lost. An example of a light protection filter from this compound class which is available commercially is 4-(tert-butyl)-4'-methoxydibenzoylmethane, which has the structure given in formula IV.

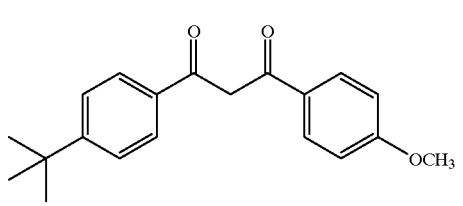

Surprisingly, it has now been found that 2-arylbenzimidazolesulfonic acids prepared according to the invention have a very good stabilizing action for the dibenzoylmethanes, in particular 4-(tert-butyl)-4-methoxybenzoylmethane. By incorporating mixtures of these compounds into cosmetics, it is now possible to prepare light protection compositions using dibenzoylmethanes which show no or only a low decrease in the protective action against UV rays, even in the case of a relatively long period of solar action, for example during sunbathing for a number of hours.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 100 30 664.0, filed Jun. 23, 2000 is hereby incorporated by reference.

EXAMPLES

The examples below illustrate the present invention in more detail without limiting the scope of the invention. The following trade names are used in the example formulations:
Antaron® V-220 is sold by GAF, Frechen, DE,
Carbomer Ultrez-10 is supplied by Goodrich, Neuss, DE,
Dehymuls® E is a mixture of dicocoylpentaerythritol citrate, sorbitol sesquioleate, beeswax and aluminium stearate and is sold by Cogni, Roermond, NL,
Eusolex® 2292, Eusolex® 232, Eusolex® 6300 and Eusolex® HMS are UV filters sold by Merck KGaA, Darmstadt, DE,
Luvitol® EHO is sold by BASF AG, Ludwigshafen, DE,
Pemulen® TR-1 and Pemulen® TR-2 are acrylate/alkyl acrylate polymers sold by Goodrich, Neuss, DE,
Performa® V825 is a synthetic wax sold by New Phase, NJ08554, US,
Oxynex® K is a mixture of PEG-8, tocopherol, ascorbyl palmitate, ascorbic acid and citric acid and is sold by Merck KGaA, Darmstadt, DE.

The sulfonic acids given in formulation examples 3 to 9 (2-phenylbenzimidazole-4,6-disulfonic acid, 1,4-bis(2-benzimidazoloyl)benzene-4,4'-6,6'-tetrasulfonic acid, 1,4-bis(2-benzimidazoloyl)benzene-5,5'-disulfonic acid) were prepared by the process according to the invention.

Example 1
Preparation of 2-phenylbenzimidazole-4,6-disulfonic Acid
108 parts of o-phenylenediamine are introduced into 500 parts of $H_2SO_4$ (>96%) and then 800 parts of oleum (65%) are added dropwise, the temperature being maintained at a maximum of 120° C. After 15 min, the mixture is cooled to 70° C. and 120 parts of benzoic acid are added. The mixture is then heated for 2 h at 180° C. The mixture is then slowly hydrolysed with 2 500 parts of water, the temperature being maintained below 10° C. The precipitate (crystals) is filtered off with suction, suspended in 8 parts of water and dissolved with sodium hydroxide solution (32%) at pH =7. The solution is stirred with activated carbon until colorless, and then precipitation is induced using 96% $H_2SO_4$ at pH=1–2. 300 parts of 2-phenylbenzimidazole-4,6-disulfonic acid are obtained. The compound has an absorption maximum in the UV-B region at $\lambda_{max}$=308 nm.

The following are prepared analogously:
2-(4'-methoxyphenyl)benzimidazole-4,6-disulfonic acid
2-(3'-methoxyphenyl)benzimidazole-4,6-disulfonic acid
2-(4'-ethoxyphenyl)benzimidazole-4,6-disulfonic acid
2-(3'-ethoxyphenyl)benzimidazole-4,6-disulfonic acid
2-(3'-5'-dimethoxyphenyl)benzimidazole-4,6-disulfonic acid
2-(3'-5'-diethoxyphenyl)benzimidazole-4,6-disulfonic acid
2-(3'-4'-diethoxyphenyl)benzimidazole-4,6-disulfonic acid
2-(2'-naphthyl)benzimidazole-4,6-disulfonic acid.

Example 2
Preparation of 1,4-bis(2-benzimidazoloyl)-benzene-4,4',6,6'-tetrasulfonic Acid 108 parts of o-phenylenediamine are introduced into 500 parts of $H_2SO_4$ (>96%) and then 800 parts of oleum (65%) are added dropwise, the temperature being maintained at a maximum of 120° C. After 15 min, the mixture is cooled to 70° C. and 83 parts of terephthalic acid are added. The mixture is then heated at 180° C. for 2 h. The mixture is then slowly hydrolysed with 2 500 parts of water, the temperature being maintained below 10° C. The precipitate (crystals) is filtered off with suction, suspended in 8 parts of water and dissolved with sodium hydroxide solution (32%) at pH 7. The solution is stirred with activated carbon until colorless, and then precipitation is induced using 96% $H_2SO_4$ at pH=1–2. 270 parts of 1,4-bis(2-benzimidazoloyl)benzene-4,4',6,6'-tetrasulfonic acid are obtained. The compound has absorption maxima at $\lambda_{max}$=208 nm, 257 nm and 335 nm.

The following compounds are prepared analogously:
1,4-bis(2-benzimidazoloyl)-3-methoxybenzene-4,4',6,6'-tetrasulfonic acid
1,4-bis(2-benzimidazoloyl)-3,5-dimethoxybenzene-4,4',6,6'-tetrasulfonic acid
1,4-bis(2-benzimidazoloyl)-3-ethoxybenzene-4,4',6,6'-tetrasulfonic acid Example 3
Sunscreen Spray (O/W)

| Phase | Ingredient | % by wt. |
| --- | --- | --- |
| A | Eusolex ® 2292 (Art. No. 105382) | 7.50 |
|   | Eusolex ® HMS (Art. No. 111412) | 7.00 |
|   | Steareth-2 | 0.40 |
|   | Steareth-10 | 0.80 |
|   | Pemulen ® TR-2 | 0.18 |
|   | Propylene glycol isoceteth-3 acetate | 5.00 |
|   | Performa ® V 825 | 0.80 |
|   | Dimethicone | 1.00 |
|   | Oxynex ® K (Art. No. 108324) | 0.10 |

-continued

| Phase | Ingredient | % by wt. |
|---|---|---|
| B | 2-Phenylbenzimidazole-4,6-disulfonic acid | 1.00 |
| | Triethanolamine | 0.90 |
| | 1, 2-Propanediol | 2.00 |
| | Preservative | 0.50 |
| | Water, demineralized | ad 100.00 |

Preparation:

Phase B:

The water is mixed with the triethanolamine and then the 2-phenylbenzimidazole-4,6-disulfonic acid is added with stirring. As soon as everything has dissolved, the other constituents of Phase B are added and then the mixture is heated to 80° C.

Phase A:

The constituents of Phase A, with the exception of Pemulen® TR-2, are combined and heated to 80° C. The Pemulen® TR-2 is then added with stirring.

Preparation of the Sunscreen Composition:

Phase B is slowly added with stirring to Phase A. Following homogenization, the mixture is cooled with stirring. The preservatives used are 0.05% of propyl 4-hydroxybenzoate and 0.15% of methyl 4-hydroxybenzoate.

Example 4

Sunscreen Spray (O/W)

| Phase | Ingredient | % by wt. |
|---|---|---|
| A | Eusolex ® 2292 (Art. No. 105382) | 7.50 |
| | Eusolex ® HMS (Art. No. 111412) | 7.00 |
| | Steareth-2 | 0.40 |
| | Steareth-10 | 0.80 |
| | Pemulen ® TR-2 | 0.18 |
| | Propylene glycol isoceteth-3 acetate | 5.00 |
| | Performa ® V 825 | 0.80 |
| | Dimethicone | 1.00 |
| | Oxynex ®K (Art. No. 108324) | 0.10 |
| B | 2-Phenylbenzimidazole-4,6-disulfonic acid | 1.00 |
| | 1,4-Bis(2-benzimidazoloyl)benzene-4,4',6,6'-tetrasulfonic acid | 1.00 |
| | Triethanolamine | 0.90 |
| | 1,2-Propanediol | 2.00 |
| | Water, demineralized | ad 100.00 |

Preparation:

Phase B:

The water is mixed with the triethanolamine and then the 1, 4-bis (2-benzimidazoloyl)benzene-4,4',6,6'-tetrasulfonic acid and the 2-phenylbenzimidazole-4,6-disulfonic acid are added with stirring. As soon as everything has dissolved, the other constituents of Phase B are added and then the mixture is heated to 80° C.

Phase A:

The constituents of Phase A, with the exception of Pemulen® TR-2, are combined and heated to 80° C. The Pemulen® TR-2 is then added with stirring.

Preparation of the Sunscreen Composition:

Phase B is slowly added with stirring to Phase A. After homogenization, the mixture is cooled with stirring. The preservatives used are 0.05% of propyl 4-hydroxybenzoate and 0.15% of methyl 4-hydroxybenzoate.

Example 5

Sunscreen Gel (Aqueous)

| Phase | Ingredient | % by wt. |
|---|---|---|
| A | 1,4-Bis(2-benzimidazoloyl)benzene-4,4',6,6'-tetrasulfonic acid | 1.00 |
| | Eusolex ®232 (Art. No. 105372) | 4.00 |
| | Sodium hydroxide solution | 6.00 |
| | Glycerol | 3.00 |
| | 1,2-Propanediol | 2.00 |
| | Preservative | q.s. |
| | Water, demineralized | ad 100.00 |
| B | Carbomer Ultrez-10 | 0.70 |
| | Water, demineralized | 60.00 |
| C | Sodium hydroxide solution (10%) | 1.50 |
| | Water, demineralized | 4.00 |

Preparation:

Carbomer Ultrez-10 is completely dispersed in the water of Phase B. Phase C is then slowly added and the mixture is homogenized.

For the Phase A, the water is firstly added to the sodium hydroxide solution and then the Eusolex® 232 is added and completely dissolved with stirring. After a clear solution has been obtained, the other constituents of Phase A are added. Phase A is then added in portions to the mixture of Phases B and C, the mixture being homogenized after each addition.

The preservative used is:

0.20% of methyl 4-hydroxybenzoate

Example 6

Sunscreen Gel (O/W)

| Phase | Ingredient | % by wt. |
|---|---|---|
| A | Eusolex ® 6300 (Art. No. 5385) | 0.75 |
| | Luvitol ® EHO | 10.00 |
| | Dimethicone | 2.00 |
| | Shea butter | 5.00 |
| | Antaron ® V-220 | 2.00 |
| | Oxynex ® K | 1.00 |
| B | 1,4-Bis(2-benzimidazoloyl)benzene-5,5'-disulfonic acid | 1.00 |
| | Eusolex ®232 (Art. No. 105372) | 0.75 |
| | Tris (hydroxymethyl) aminomethane | 0.33 |
| | Preservative | q.s. |
| | Water, demineralized | 20.00 |
| C | Tris (hydroxymethyl) aminomethane | 1.20 |
| | Water, demineralized | 10.00 |
| D | Pemulen ® TR-1 | 0.60 |
| | Water, demineralized | ad 100.00 |

Preparation:

The Pemulen® TR-1 is dissolved in the water of Phase D. The tris(hydroxymethyl)aminomethane is dissolved in the water of Phase C and the solution is added to Phase D. The tris(hydroxymethyl)aminomethane is dissolved in the water of Phase B and then, with stirring, the Eusolex® 232 is added. After a clear solution has been obtained, the other constituents of Phase B are added and then Phase B is added to the mixture of Phases C and D and homogenized. The constituents of Phase A are combined and heated. Phase D is then added to the mixture of the other phases with homogenization.

The preservatives used are 0.05% of propyl 4-hydroxybenzoate and 0.15% of methyl 4-hydroxybenzoate.

Example 7
Sunscreen Gel (O/W)

| Phase | Ingredient | % by wt. |
|---|---|---|
| A | Eusolex ® 6300 (Art. No. 5385) | 0.75 |
|   | Luvitol ® EHO | 10.00 |
|   | Dimethicone | 2.00 |
|   | Shea butter | 5.00 |
|   | Antaron ® V-220 | 2.00 |
|   | Oxynex ® K liquid (Art. No. 8324) | 1.00 |
| B | 2-Phenylbenzimidazole-4,6-disulfonic acid | 1.00 |
|   | 1,4-Bis(2-benzimidazoloyl)benzene-4,4',6,6'-tetrasulfonic acid | 0.75 |
|   | Tris (hydroxymethyl) aminomethane | 0.33 |
|   | Preservative | q.s. |
|   | Water, demineralized | 20.00 |
| C | Tris (hydroxymethyl) aminomethane | 1.20 |
|   | Water, demineralized | 10.00 |
| D | Pemulen ® TR-1 | 0.60 |
|   | Water, demineralized | ad 100.00 |

Preparation:

The Pemulen® TR-1 is dissolved in the water of Phase D. The tris(hydroxymethyl)aminomethane is dissolved in the water of Phase C and the solution is added to Phase D. The tris(hydroxymethyl)aminomethane is dissolved in the water of Phase B and then the 2-phenylbenzimidazole-4,6-disulfonic acid and the 1,4-bis(2-benzimidazoloyl)benzene-4,4',6,6'-tetrasulfonic acid is added with stirring. After a clear solution has been obtained, the other constituents of Phase B are added, and then Phase B is added to the mixture of Phases C and D and homogenized. The constituents of Phase A are combined and heated. Phase A is then added to the mixture of the other phases with homogenization.

The preservatives used are 0.05% of propyl 4-hydroxybenzoate and 0.15% of methyl 4-hydroxybenzoate.

Example 8
Sunscreen Lotion (W/O) with UVA/B Protection

| Phase | Ingredient | % by wt. |
|---|---|---|
| A | Eusolex ® 2292 (Art. No. 105382) | 3.00 |
|   | Eusolex ® 4360 (Art. No. 105376) | 2.00 |
|   | Dehymuls ® E | 6.00 |
|   | Hydrogenated castor oil | 1.00 |
|   | Beeswax | 2.00 |
|   | Oleyl erucate | 6.00 |
|   | Decyl oleate | 6.00 |
|   | Dimethicone | 1.00 |
|   | Dicapryl ether | 5.00 |
| B | Glycerol (87%) | 5.00 |
|   | 1,4-Bis(2-benzimidazoloyl)benzene-4,4',6,6'-tetrasulfonic acid | 3.00 |
|   | Magnesium sulfate heptahydrate | 1.00 |
|   | Preservative | q.s. |
|   | Water, demineralized | ad 100.00 |

Preparation:

The constituents of Phases A and B are each combined. Phase A is heated to 75° C. and Phase B is heated separately to 80° C. Phase B is added to Phase A with homogenization. The mixture is then cooled with stirring.

The preservatives used are:
0.05% of propyl 4-hydroxybenzoate
0.15% of methyl 4-hydroxybenzoate.

Example 9
Sunscreen Lotion (W/O) with UVA/B Protection

| Phase | Ingredient | % by wt. |
|---|---|---|
| A | Eusolex ® 2292 (Art. No. 105382) | 3.00 |
|   | Eusolex ® 4360 (Art. No. 105376) | 2.00 |
|   | Dehymuls ® E | 6.00 |
|   | Hydrogenated castor oil | 1.00 |
|   | Beeswax | 2.00 |
|   | Oleyl erucate | 6.00 |
|   | Decyl oleate | 6.00 |
|   | Dimethicone | 1.00 |
|   | Dicapryl ether | 5.00 |
| B | 2-Phenylbenzimidazole-4,6-disulfonic acid | 2.00 |
|   | 1,4-Bis(2-benzimidazoloyl)benzene-5,5'-disulfonic acid | 2.00 |
|   | Glycerol (87%) | 5.00 |
|   | Magnesium sulfate heptahydrate | 1.00 |
|   | Preservative | q.s. |
|   | Water, demineralized | ad 100.00 |

Preparation:

The constituents of Phases A and B are each combined. Phase A is heated to 75° C. and, separately, Phase B is heated to 80° C. Phase B is added to Phase A with homogenization. The mixture is then cooled with stirring.

The preservatives used are:

0.05% of propyl 4-hydroxybenzoate
0.15% of methyl 4-hydroxybenzoate.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for the preparation of 2-arylbenzimidazolesulfonic acid of the formula:

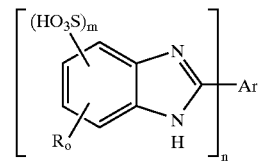

I wherein

Ar is a substituted or unsubstituted phenyl or naphthyl radical and

R is a $C_{1-8}$-alkyl radical or a $C_{1-8}$-alkoxy radical n is 1, 2, 3 or 4, in is 2 or 3 and o is 0, 1 or 2, comprising reacting an o-phenylenediamine according in the formula II

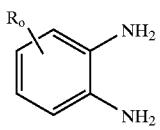

with a second compound having the formula III:

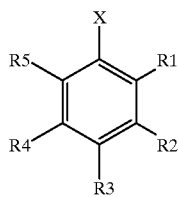

in the presence of sulphuric acid activated with oleum, and at a temperature of 20° C. to 200° C., wherein R1, R2, R3, R4 and R5 are each independently of one another a radical selected from H, $C_{1-8}$-alkyl, $C_{1-8}$-alkoxy, hydroxyl, nitro, F, Cl, Br, I, COOH, COOR', COCl, COBr or CN, R1 and R2 together or R2 and R3 together are optionally a fused-on, optionally substituted phenylene unit, and R' is a $C_{1-20}$-alkyl radical, and X is a radical selected from —COOH, —COOR', —COCl, —COBr, or —CN.

2. A method according to claim 1, wherein X of compound III is a —COOH group or a —COOR' group, wherein R' is a $C_{1-20}$-alkyl radical.

3. A method according to claim 1, wherein R1 and R2 of formula III together form a fused-on, optionally substituted phenylene unit.

4. A method according to claim 1, wherein R2 and R3 in formula III together form a fused-on, optionally substituted phenylene unit.

5. A method according to claim 1, wherein the reaction takes place at a temperature from 160° C. to 190° C.

6. A method according to claim 1, wherein X in formula III is a —COOR' group where R' is a $C_{1-8}$-alkyl radical.

7. A method according to claim 1, wherein X in formula III is a —COOR' group where R' is a methyl or ethyl radical.

8. A method according to claim 1, wherein compound III is benzoic acid, salicylic acid, phthalic acid, terephthalic acid, isophthalic acid, 1,2,3-benzenetricarboxylic acid, 1,2,4-benzenetricarboxylic acid, 1,3,5-benzenetricarboxylic acid, 1,2,4,5-benzenetetracarboxylic acid, 1-naphthalenecarboxylic acid, 2-naphthalenecarboxylic acid, or 3-naphthalenecarboxylic acid.

9. A method according to claim 1, wherein compound III is benzoic acid, terephthalic acid, phthalic acid or 1,3,5-benzenetricarboxylic acid.

10. A method according to claim 1, wherein the reaction is carried out from 2 to 8 hours.

11. A method according to claim 1, wherein the sulphuric acid is a provided as a 50–100% sulphuric acid solution.

12. The method of claim 1, wherein the oleum is provided as a 65% solution of sulfur trioxide in sulphuric acid.

13. The method of claim 1, which comprises combining the sulphuric acid and o-phenylenediamine, activating with oleum at a temperature below 150° C., cooling to a temperature below 100° C. and adding the second reactant, then, heating to a temperature of from 150–250° C. for the reaction and hydrolyzing.

* * * * *

UNITED STATES PATENT AND TRADEMARK OFFICE
CERTIFICATE OF CORRECTION

PATENT NO. : 6,593,476 B2
DATED : July 15, 2003
INVENTOR(S) : Ulrich Heywang et al.

It is certified that error appears in the above-identified patent and that said Letters Patent is hereby corrected as shown below:

Column 18,
Line 66, reads "in is 2 or 3" should read -- m is 2 or 3 --

Signed and Sealed this

Twenty-second Day of June, 2004

JON W. DUDAS
*Acting Director of the United States Patent and Trademark Office*